United States Patent [19]

Raskin

[11] Patent Number: 4,659,311

[45] Date of Patent: Apr. 21, 1987

[54] APPARATUS FOR MAKING DENTURE

[76] Inventor: Paul D. Raskin, 1600 39th St., Sacramento, Calif.

[21] Appl. No.: 772,140

[22] Filed: Sep. 3, 1985

[51] Int. Cl.$^4$ .................................................. A61C 11/00
[52] U.S. Cl. ...................................... 433/55; 249/54; 264/17; 425/3; 433/54
[58] Field of Search .................. 249/54, 55; 425/2, 3, 425/DIG. 11; 264/16, 17, 18; 433/34, 57, 213, 55, 56, 60, 54

[56] References Cited

U.S. PATENT DOCUMENTS

| | | | |
|---|---|---|---|
| 1,517,922 | 12/1924 | Stanley | 433/57 |
| 2,003,727 | 6/1935 | Tofflemire | 433/55 |
| 2,171,759 | 9/1939 | Meyer | 433/213 |
| 2,748,481 | 6/1956 | Glueck | 433/56 |
| 3,221,408 | 12/1965 | Scullin | 433/60 |
| 3,653,126 | 4/1972 | Hansen | 433/60 |
| 4,337,039 | 6/1982 | Martin et al. | 433/34 |
| 4,501,556 | 2/1985 | Zelnigher | 433/60 |

FOREIGN PATENT DOCUMENTS

| | | | |
|---|---|---|---|
| 707155 | 4/1965 | Canada | 433/57 |
| 2725683 | 12/1977 | Fed. Rep. of Germany | 433/60 |

*Primary Examiner*—Jay H. Woo
*Assistant Examiner*—James C. Housel
*Attorney, Agent, or Firm*—Mark C. Jacobs

[57] ABSTRACT

Apparatus for making dentures comprising a base, an articulating member pivotally mounted to the base and adjustable with respect thereto, magnets on the base adapted to hold a metal plate in a fixed position on the base, and a probe on the articulating member for spacing the articulating member a predetermined distance above the base. Measurements are taken on a patient's mouth and his preexisting dentures are placed on the plate. Plaster of paris or other suitable material is placed on the articulating member in a non-solidified state and retained thereto. The measurements taken are used to adjust the probe and the relation of the dental cast to the plate, and the denture may be raised or lowered with respect to the base, using loose magnets and shims, to provide the desired position and angularity to the denture. When the articulating member is pivoted into a position engaging the denture on the plate, a cast of the upper portion of the denture containing therein an impression of the patient's edentulous ridge is thereby related to the proposed occlusal plane. This mounted cast can then be used to make dentures by techniques well known in the art.

11 Claims, 8 Drawing Figures

APPARATUS FOR MAKING DENTURE

BACKGROUND OF THE INVENTION

1. Field of the Invention

The invention relates to denture making apparatus; and, more particularly, to apparatus for relating a cast of a denture to a proposed occlusal plane.

2. Description of the Prior Art

Various devices are known in the art for forming casts of dentures. Generally speaking, such devices merely form a cast of a denture without taking into consideration the occlusal plane of the patient. A considerable amount of manual work must be made in order to reproduce a denture having the patient's exact measurements. Reference must be made back to the patient. Thus, such prior art techniques involve considerable trial and error and reference back to the patient to see if the dentures being reproduced are proper. Also, such prior art devices do not provide for means for changing the orientation of a denture being reproduced so as to make new dentures having different dimensional relationships.

There thus is a need for apparatus that can be used to reproduce dentures for a patient taking into consideration the patient's jaw measurements, including the occlusal plane of the patient.

SUMMARY OF THE INVENTION

It is an object of this invention to provide improve apparatus for producing dentures.

It is a further object of this invention to provide denture forming apparatus which takes into consideration the occlusal plane of the patient.

It is still another object of the invention to provide denture forming apparatus having a base with a plate held in position on the base but vertically and angularly adjustable thereon, with an articulating member adapted to hold plaster of paris and pivotable into a position engaging a denture disposed on the plate.

These and other objects are preferably accomplished by providing a base, an articulating member pivotally mounted to the base and adjustable with respect thereto, magnets on the base adapted to hold a metal plate in fixed position on the base, and a probe on the articulating member for spacing the articulating member a predetermined position above the base. Measurements are taken of a patient's mouth with reference to his existing denture and his preexisting dentures are placed on the plate. Plaster of paris or other suitable material in the non-solidified state or otherwise not set is mounted to the articulating member and retained thereon. The measurements taken are used to adjust the probe and the plate, and the denture may be raised or lowered with respect to the base, using loose magnets and shims, to provide the desired angularity to the denture. When the articulating member is pivoted into a position engaging the denture on the plate, a case of the upper portion of the denture is related to the proposed occlusal plane. This cast may then be used for making dentures by techniques well known in the art.

DESCRIPTION OF THE PREFERRED EMBODIMENT

Figure 1:
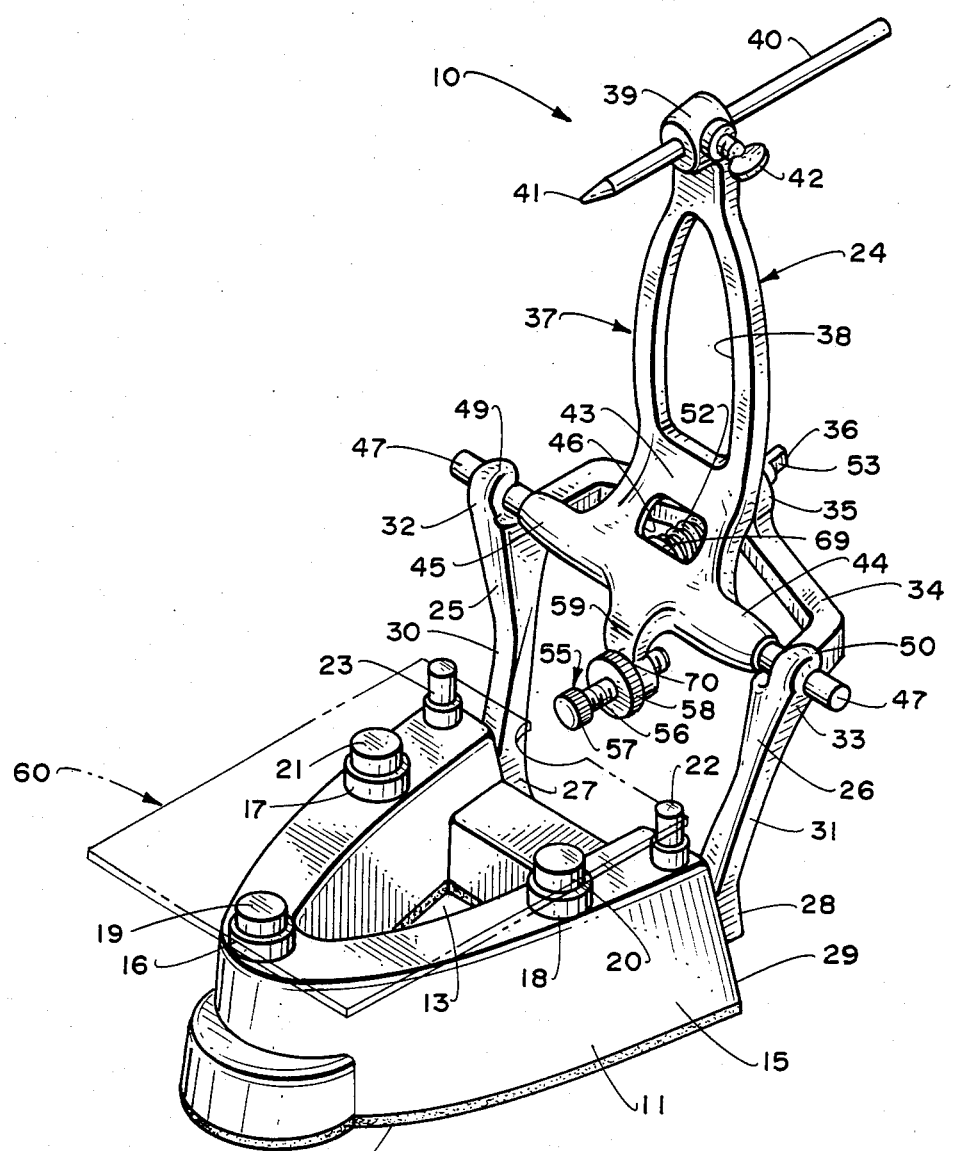
FIG. 1 is a perspective view of apparatus for making dentures in accordance with the teachings of the invention.
Figure 2:
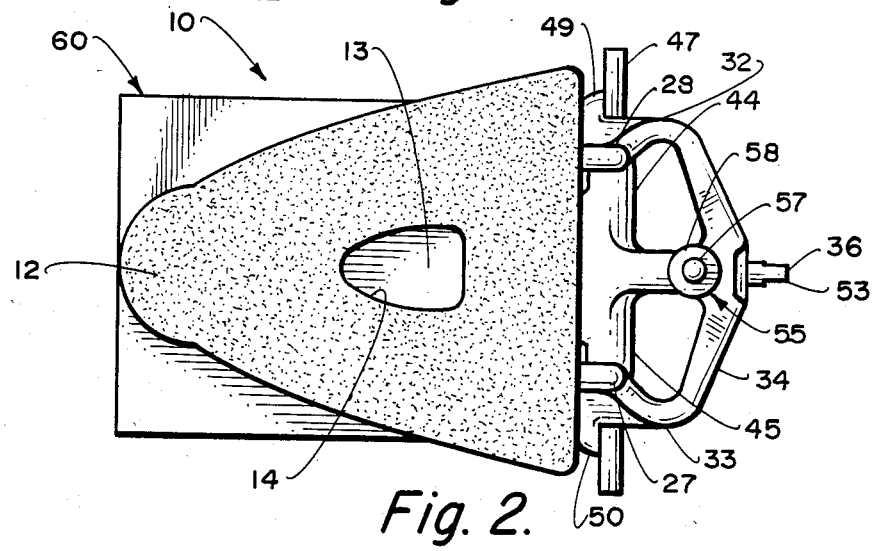
FIG. 2 is a bottom view of the apparatus of FIG. 1.
Figure 3:
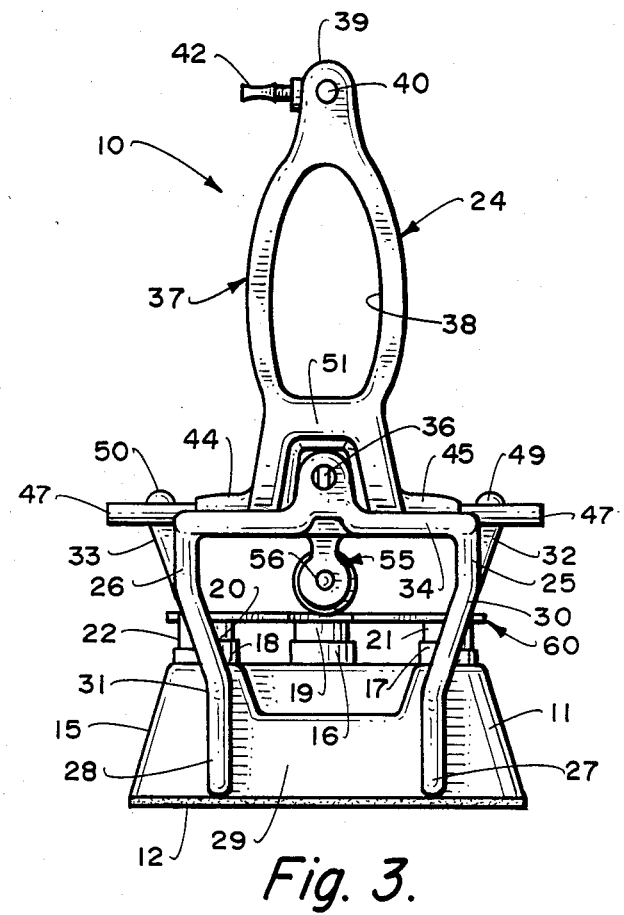
FIG. 3 is a rear view of the apparatus of FIG. 1.

Referring now to FIG. 1 of the drawing, a device 10 is shown which is used in making dentures. Device 10 includes a main base 11 which, as seen particularly in FIG. 2, is generally triangular-shaped having a flat bottom surface 12 with an arcuate cut-out section 13 along linear edge 14 thereof. As seen in FIG. 3, base 11 has a tapered peripheral side 15 and the portion of base 11 at cut-out section 13 is lower in height than the remainder of base 11 optionally bottom 12 may be filled and felt covered.

A plurality of bosses, such as the three shown in FIG. 1 e.g. bosses 16 to 18, are provided at each one of the apices of base 11 on the upper surface thereof. As seen in FIG. 1, these bosses 16 to 18 have circular depressions loosely receiving therein a magnet, such as magnets 19 to 21, respectively. In addition, the upper surfaces of bosses 16 to 18 are also of magnetic material for reasons to be discussed. Rearwardly of each of the bosses 17, 18 a pair of vertically extending metal guide posts 22, 23 are provided on the upper surface of base 11.

An articulating member 24 is mounted to base 11. As particularly seen in FIGS. 2 and 3, member 24 includes a pair of vertical arms 25, 26 having bracket portions 27, 28 fixedly mounted to the rear wall 29 of base 11. Arms 25, 26 have first lower portions 30, 31 respectively extending upwardly from bracket portions 27, 28 with integral outwardly extending upper portions 32, 33 interconnected at the top by a U-shaped connecting bracket 34.

Bracket 34 has a central apertured boss 35 (see particularly FIG. 3) receiving a screw 36 therethrough (FIG. 1).

Articulating member 24 includes an articulating portion 37 (see also FIG. 3) comprised of an elongated oval shaped member having a centrally located oval or wishbone-shaped opening 38 with an extension portion 39 extending from the apex of the opening 38 as seen in FIG. 3.

As seen in FIG. 1, an incisal reference pin or probe 40, having a tapered probe point or tip 41, is mounted in a vertical aperture in extension portion 39. A thumb screw 42 (Fig.3) is threaded in a threaded aperture in extension portion 39, extending normal to the vertical aperture in which probe 40 is mounted, so that screw 42 can be selectively tightened against probe 40 to retain it in extension portion 39, or loosened to allow removal of probe 40, or the vertical adjustment thereof.

As seen in FIGS. 1 and 3, portion 37 has a rearwardly downwardly sloping portion 43, extending from opening 38 (FIG. 1) with outwardly extending bosses 44, 45 on each side of portion 43 extending parallel to the elongated leg 48 of bracket 34. These bosses 44, 45 are apertured and aligned with a like opening in the rear arm 51 (FIG. 4) of sloping portion 43 (which has a cut-out portion 46 - FIG. 3) the extending bosses 44, 45 each have pins 47 at both ends as a part of said extending bosses 44, 45, such as a metal pin, which also extends parallel to the elongated leg 48 of bracket 34. As seen in FIGS. 1 and 3, the upper portions 32, 33 of arms 25, 26, respectively, are preferably bifurcated forming branches 49, 50 respectively, which curve at the top, as shown in FIGS. 1 and 3, loosely trapping therein the pin 47 so that pin 47 is rotatable therein.

Figure 4:
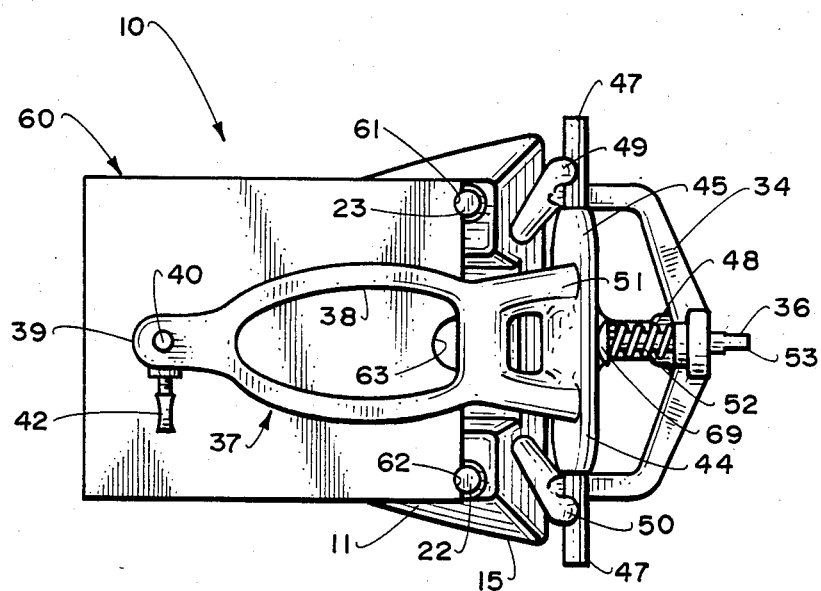
FIG. 4 is a top plan view of the apparatus with articulating member shown in down position.

Thus, the articulating portion 37 pivots on pin 47 within branches 49, 50 see also FIG. 4.

As shown in FIG. 4, screw 36 has a head 69 abutting against the midpoint of rear arm 51, sliding in the opening in leg 48 (and enlarged at end 53 which acts as a stop). Since head 69 loosely abuts against arm 51, pulling back on spring 52 allows disengagement of head 69 from contact with arm 51 and removal of portion 37.

Figure 5:
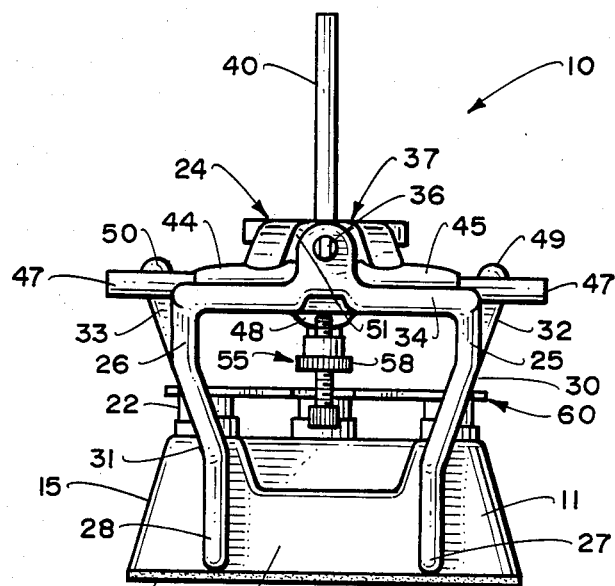
FIG. 5 is a rear vertical view with articulating member shown in down position.

As seen in FIG. 5, a screw 55 is threaded in an aperture in an extension portion 59 extending rearwardly and downwardly from the rear arm 51 of portion 37. Screw 55 has a main threaded body 56 and a screw head 57. A knurled adjusting nut 58 is threaded on body 56 between portion 59 and head 57. The free or upper end of screw 55 bears against a boss 70 on arm 51 (FIG. 5).

It can be appreciated that knurled nut 58 can be adjusted to bear against portion 59 and against boss 70 thus raising articulating portion 37 (or loosened to lower portion 37) allowing for vertical adjustment which simulates the jaw hinge of a patient.

Figure 6:
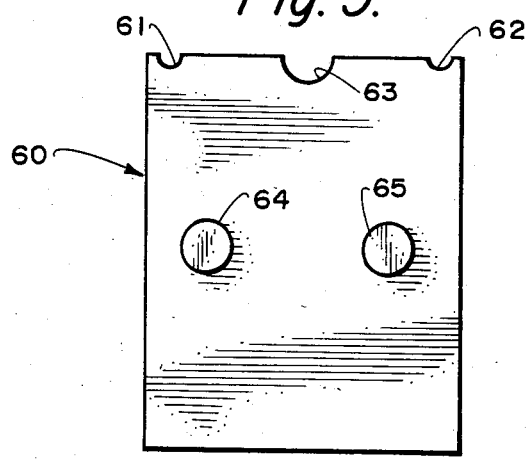
FIG. 6 is a plan view of a metal plate used with the device of FIGS. 1 to 5.

As seen in FIG. 6, a metal plate 60 is provided for use with device 10. Plate 60 is a generally rectangular planar member having cut-out portions at corners 61, 62. As seen particularly in FIG. 4, plate 60 is adapted to rest on top of magnets 19 to 21 (FIG. 1) with plate 60 straddling posts 22, 23 at cut-out portions 61, 62. Of course, magnets 19 to 21 may be removed and the built-in magnets of bosses 16 to 18 will hold the plate 60 in position, since plate 60 is preferably made of magnetizeable steel.

Plate 60 may need a cut-out zone 63 at the rear allowing for screw 55 to enter therein when plate 60 is mounted on base 11 if plate 60 is overly deep. Of course, the overall length of screw 55 may be shortened so as to clear the plate or plate 60 may be moved forwardly on base 11 to allow for clearance. See FIG. 6.

The articulating member 24 may be of brass and the base or support 11 (except for the magnetic material of bosses 16 to 18) may be of a cast resin material. Plate 60 may be of steel. The magnets 19 to 21 and the magnetic material of bosses 16 to 18 may be heavy magnets of samarium cobalt. Guide posts 22, 23 may be of any suitable metallic material as is probe 40. As seen in FIG. 6, other loosely disposed disk-shaped magnets 64, 65, similar to magnets 19 to 21, may be provided on top of plate 60 and, as will be discussed may be placed anywhere on top of plate 60.

Figure 7:
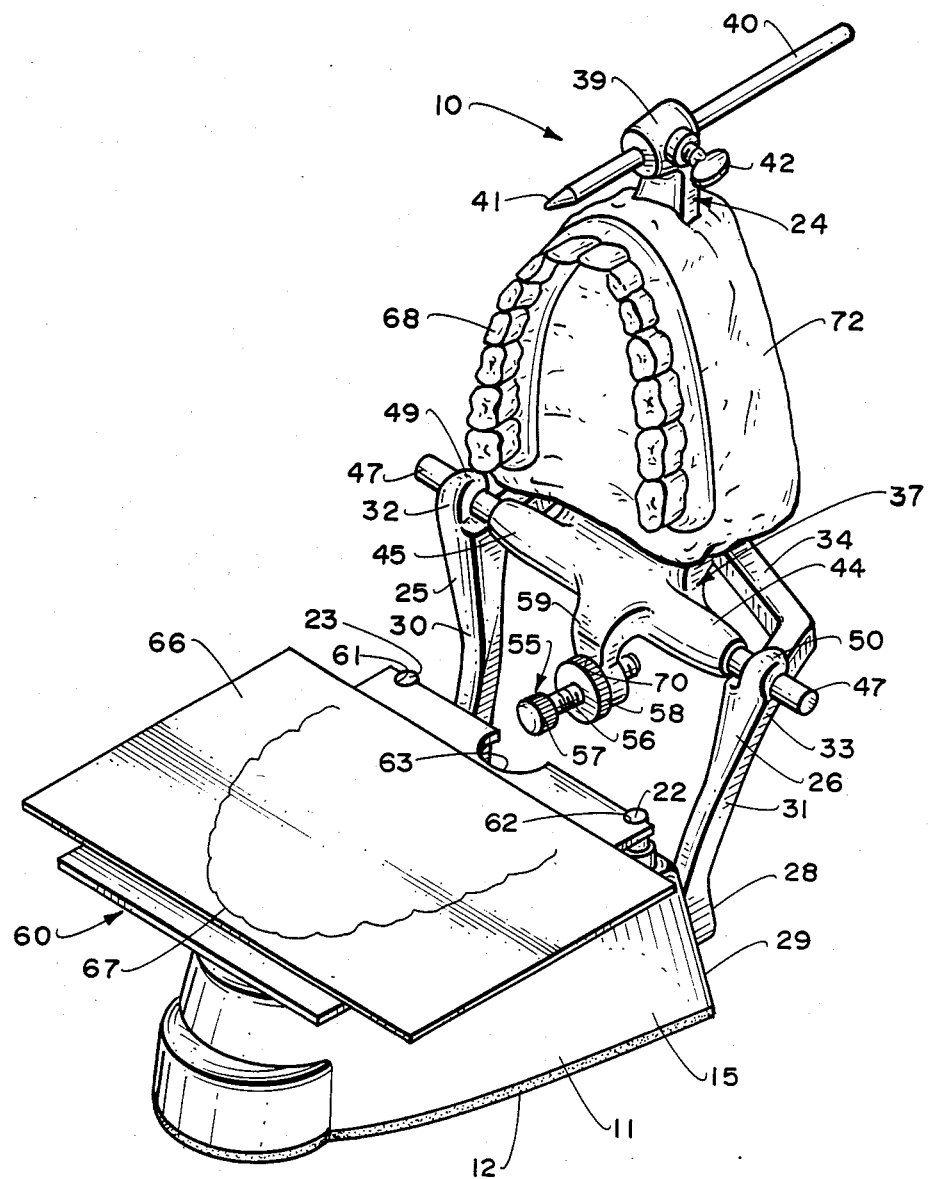
FIG. 7 is a perspective view of apparatus with paper and denture.

In operation, the apparatus is set up as in FIG. 1, articulating portion 37 shown as raised with a piece of paper 66 (FIG. 7) having indicia 67 thereon relating to the measurements of the occlusal plane of the patient's mouth and other important parameters and measurements. An outline of the patient's preexisting denture, such as his upper denture, may be provided on paper 66. The patient's preexisting upper denture 68 is now placed on the paper 66 (of course, paper 66 can be removed, if desired).

Figure 8:
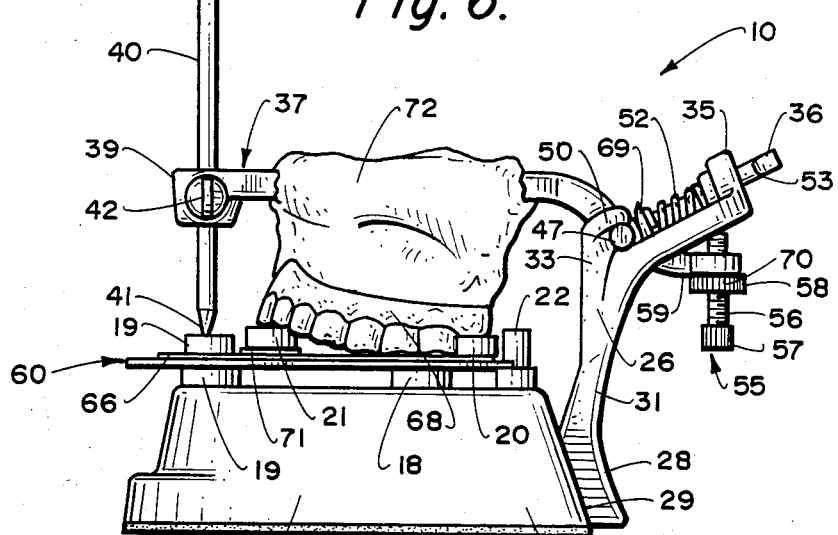
FIG. 8 is a side view of apparatus with paper, magnets and denture.

As seen in FIG. 8, magnets, such as magnets 19 to 21 are used on top of plate 60. Magnet 19, for example, is placed under the tip 41 of probe 40 and probe 40 is adjusted, via screw 42, to provide a predetermined height between articulating portion 37 and plate 60.

Magnets 20 and 21 are placed under denture 68 to build it up at the locations illustrated in accordance with the parameters recorded on paper 66. Additionally, one or more shims 71 may be used such as between magnet 21 and plate 60, to provide the desired angular relation to he denture 68 on plate 60. Of course, shims and magnets need not be used if the correct angle is present.

Quick drying plaster of paris or other suitable casting material 72 is now molded onto articulating portion 37, on the portion thereof surrounding opening 38 and in opening 38 to retain in place a newly made cast of the patient's mouth said cast having been made of gypsum or other suitable matter, in the articulator in order to orient said cast in the proposed occlusal plane. The articulating portion 37 is now pivoted downwardly from the FIG. 7 position to the FIG. 8 position.

Thus with the location of the upper teeth for the denture now located, a new denture can now be made by any technique available to those with skill in the art.

Probe 40 is thus adjusted to make a permanent reference for the incisal length of the new work, and a tracing can be made about the mounted denture to be used as a guide for setting teeth. Screw 57, 58 is used clinically to establish the distance between upper and lower mouth casts in making new dentures. That is, screw 57, 58 can adjust the rear pivotal end of articulating portion 37 with respect to the fixed portion of articulating member 24 thus permitting correlation of the angularity of the upper jaw of a patient with respect to the lower jaw.

It can be seen that there is disclosed an improved apparatus useful in forming dentures, which apparatus aides the dentist to make a more precise fitting denture set quicker and easier, by coordinating his or her plan for the denture with the actual product being made.

It is also seen that while a specific configuration for the hinging of the top to the base, i.e. the articulating member is disclosed herein, other hinge means, both severable and non-severable that permit the accurate measurements required for denture manufacture to be utilized, may be employed herein.

Since certain changes may be made in the above apparatus without departing from the scope of the invention herein involved, it is intended that all matter contained in the above description and shown in the accompanying drawings shall be interpreted as illustrative and not in a limiting sense.

I claim:
1. Apparatus for reproducing dentures including:
a main base having a trio of first magnetic means fixedly disposed on the upper surface thereof at a trio of spaced locations thereon adapted to magnetically attract a magnetic metallic plate;
a metallic plate loosely disposed on the upper surface of said base and magnetically held thereto by said magnetic means;
guide means associated with both said base and said plate for aligning said plate in a predetermined position on said base;
an articulating member fixedly secured to said base having a main support extending upwardly from said base and fixed thereto, said articulating member including an articulating portion pivotally mounted to said main support extending outwardly over the upper surface of said base and spaced therefrom when in a first position and pivotable to a second position extending generally normal to the plane of the upper surface of said base;

a trio of second movable magnetic means adapted to be both interposed between said first magnetic means and said plate; and adapted to be magnetically mounted on the top of said plate, and a probe carried at the forward end of said articulating portion at a point thereon away from the pivot point thereof to said main support, said probe being vertically adjustable with respect to said articulating portion and extending vertically downwardly generally normal to the plane of the upper surface of said base when said articulating portion is in said first position, said probe terminating at its lower end in a point adapted to abut against the upper surface of said base when said plate is removed therefrom wherein the trio of second magnetic means are adapted and employed to orient a denture-based cast of the user's jaw configuration, using coordinates designated on the denture-based cast, to the proposed occlusal plane for the correct construction of a new denture.

2. In the apparatus of claim 1 wherein said first magnetic means includes a trio of circular bosses on the upper surface of said base forming circular cavities, said bosses being of metallic material.

3. In the apparatus of claim 2 wherein the upper surface of said base is generally triangularly shaped with said bosses being disposed at the apices of said triangle.

4. In the apparatus of claim 3 wherein said guide means includes vertical spaced posts on said base rearwardly of said bosses adjacent the point of connection of said main support to said base, said guide means further including cut-out portions in said plate adapted to straddle said posts when said plate is disposed on said base.

5. In the apparatus of claim 1 wherein said articulating portion includes an oval-shaped member having an elliptical opening therethrough.

6. In the apparatus of claim 1 wherein the pivotal connection of said articulating portion to said main support is adjustable to alter the range of motion.

7. In the apparatus of claim 1 wherein said main support includes a U-shaped bracket fixed at the top thereof, and a spring-biased screw having a main shaft extending through said bracket away from said base and a head abutting against said articulating portion, a spring encircling said screw between said head and said bracket.

8. In the apparatus of claim 7 wherein said main support includes a pair of spaced upwardly extending arms, each of said arms being bifurcated at the top thereof with said U-shaped bracket fixedly secured thereto, said articulating portion having a pin resting in said spaced bifurcated portions and retained therein and pivotal thereabout.

9. In the apparatus of claim 8 wherein said articulating portion includes a boss having a throughbore receiving said pin therethrough, a flange extending away from said boss at an angle with respect thereto, when said articulating portion is in said first position, to an elliptically-shaped member extending generally horizontally over said base having an elliptically-shaped opening therethrough, said elliptically-shaped member terminating at an extension portion receiving said probe in an aperture therein, said flange, said boss, said elliptically-shaped member and said extension portion forming said articulating portion.

10. A combination of a preformed upper denture-based cast of the user's current jaw configuration, with an apparatus for use in the manufacture of a new denture, which apparatus is used to orient said denture-based cast along the occlusal plane of the to be made new denture, which apparatus comprises:

a main base having a trio of first magnetic means fixedly disposed on the upper surface thereof at a trio of spaced locations thereon adapted to magnetically attract a magnetic metallic plate;

a metallic plate loosely disposed on the upper surface of said base and magnetically held thereto by said magnetic means;

guide means associated with both said base and said plate for aligning said plate in a predetermined position on said base;

an articulating member fixedly secured to said base having a main support extending upwardly from said base and fixed thereto, said articulating member including an articulating portion pivotally mounted to said main support extending outwardly over the upper surface of said base and spaced therefrom when in a first position and pivotable to a second position extending generally normal to the plane of the upper surface of said base;

a trio of second movable magnetic means adapted to be both interposed between said first magnetic means, and said plate; and adapted to be magnetically mounted on the top of said plate, a probe carried at the forward end of said articulating portion at a point thereon away from the pivot point thereof to said main support, said probe being vertically adjustable with respect to said articulating portion and extending vertically downwardly generally normal to the plane of the upper surface of said base when said articulating portion is in said first position, said probe terminating at its lower end in a point adapted to abut against the upper surface of said base when said plate is removed therefrom;

and retention means for retaining said upper denture-based cast on the articulating member of said apparatus, wherein the said plate is magnetically secured to said trio of first magnetic means, and the trio of second magnetic means are mounted on the top of said plate, interposed between said denture-based cast and the plate, at locations on the plate corresponding to predefined coordinates on said denture-based cast to align the cast along the proposed occlusal plane for the new denture.

11. The combination of claim 10 wherein the retention means is plaster of paris.

* * * * *